United States Patent

Diehl et al.

(10) Patent No.: US 8,828,205 B2
(45) Date of Patent: Sep. 9, 2014

(54) GAS SENSOR

(75) Inventors: Lothar Diehl, Gerlingen (DE); Thomas Seiler, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 1519 days.

(21) Appl. No.: 12/093,681

(22) PCT Filed: Oct. 16, 2006

(86) PCT No.: PCT/EP2006/067432
§ 371 (c)(1),
(2), (4) Date: Aug. 7, 2008

(87) PCT Pub. No.: WO2007/054421
PCT Pub. Date: May 18, 2007

(65) Prior Publication Data
US 2009/0152112 A1   Jun. 18, 2009

(30) Foreign Application Priority Data

Nov. 14, 2005   (DE) .......................... 10 2005 054 144

(51) Int. Cl.
*G01N 27/407*   (2006.01)
*G01N 27/419*   (2006.01)
*F02D 41/14*   (2006.01)

(52) U.S. Cl.
CPC .......... *F02D 41/1456* (2013.01); *G01N 27/419* (2013.01); *G01N 27/4072* (2013.01)
USPC ......... 204/424; 204/426; 73/23.31; 73/23.32; 205/783.5; 205/781; 205/785

(58) Field of Classification Search
USPC ...................... 204/424–429; 73/23.31–23.32; 205/783.5–785, 781
See application file for complete search history.

(56) References Cited

U.S. PATENT DOCUMENTS

| 4,629,535 | A | | 12/1986 | Oyama et al. |
| 4,718,999 | A | | 1/1988 | Suzuki et al. |
| 5,174,885 | A | * | 12/1992 | Hayakawa et al. ........... 204/425 |
| 5,507,174 | A | | 4/1996 | Friese et al. |

(Continued)

FOREIGN PATENT DOCUMENTS

| DE | 198 05 023 | 8/1999 |
| DE | 102 16 724 | 10/2003 |
| DE | 10 2004 006 875 | 9/2005 |
| EP | 0 856 732 | 8/1998 |

*Primary Examiner* — Bach Dinh
(74) *Attorney, Agent, or Firm* — Kenyon & Kenyon LLP

(57) ABSTRACT

Disclosed is a gas sensor, particularly a lambda probe, for determining the oxygen concentration in the exhaust gas of an internal combustion engine that is operated using a fuel-air mixture. Said gas sensor comprises a pump cell with an outer electrode that is exposed to the exhaust gas, an inner electrode located in a measuring chamber which is separated from the exhaust gas by means of a first diffusion barrier, and an electronic circuit for generating a voltage applied between the outer electrode and the inner electrode as well as for measuring and evaluating a pump current that is generated in said process in order to draw a conclusion therefrom about the composition of the fuel-air mixture. The inventive gas sensor is characterized in that the outer electrode is arranged in an independent measuring volume which is separated by means of an additional, second diffusion barrier whose coefficient of diffusion is different from that of the first diffusion barrier while the circuit is configured so as to preferably repeatedly reverse the polarity of the voltage.

7 Claims, 1 Drawing Sheet

(56) References Cited

U.S. PATENT DOCUMENTS

| | | | |
|---|---|---|---|
| 5,686,654 A * | 11/1997 | Friese et al. | 73/23.32 |
| 6,228,252 B1 * | 5/2001 | Miyata et al. | 205/781 |
| 2005/0252771 A1 * | 11/2005 | Wiedenmann et al. | 204/426 |
| 2007/0125648 A1 * | 6/2007 | Riegel et al. | 204/424 |

* cited by examiner

State of the Art

GAS SENSOR

TECHNICAL FIELD

The invention concerns a gas sensor according to the category of claim 1.

BACKGROUND

Electrochemical gas sensors are applied in terms of exhaust gas oxygen sensors (lambda sensors) in exhaust gas systems of combustion engines in motor vehicles, in order to provide signals over the exhaust gas composition for the motor control. Hereby the engine can be operated so, that the exhaust gases show an optimal composition for the post-treatment with the catalysts, that are usually present in an exhaust gas system nowadays.

FIG. 1 displays a gas sensor, which is known from the state of the art and pursuant to this category. The sensor element 100 presents a gas entry leak 115, through which exhaust gas flows in and arrives at a measurement chamber 130 through a diffusion barrier 120. An inner pump electrode 140 is arranged in the measurement chamber. An outer pump electrode 150, which is arranged at the outside of the solid electrolyte 110 and under a porous protective layer 155, is exposed to the exhaust gas of a (not further shown) combustion engine.

A pump voltage $U_{pump}$ is applied between the inner pump electrode 140 and the outer pump electrode 150, so that a pump current $I_{pump}$ flows. A heating device 160, which is embedded in an isolation layer 162, is furthermore arranged in the solid electrolyte 110. Via the heating device 160 the sensor element 100 is warmed up to a temperature, which allows an optimal functioning of the sensor element 100.

This planar broad-band lambda sensor according to the principle of limited current is admitted with a solid pump voltage $U_{pump}$. At a lean exhaust gas, meaning an exhaust gas with air surplus, the solid pump voltage $U_{pump}$ produces a positive pump current $I^{pump}$, which is clearly connected with the oxygen content of the exhaust gas. In a rich exhaust gas, meaning an exhaust gas with fuel surplus, there is a positive pump current as well, but due to the decomposing of the water contained in the exhaust gas.

The applied pump voltage $U_{pump}$ is indeed lying clearly under the decomposition voltage of the water, but since hydrogen exists in the exhaust gas, the water decomposition is energetically possible, because of the production of water from the reaction between hydrogen and oxygen at the outer pump electrode 150. The pump current $I_{pump}$ is thus limited at a rich exhaust gas by the hydrogen content. Since this pump current $I_{pump}$ shows the same direction in rich exhaust gas like the pump current $I_{pump}$ in a lean exhaust gas, the exhaust gas composition cannot be implied anymore from the pump current $I_{pump}$.

The task of the present invention is to improve a gas sensor pursuant to this category, so that the exhaust gas composition can be implied from a lean as well as from a rich exhaust gas.

SUMMARY

This task is solved by a gas sensor with the characteristics of claim 1. The basic idea of the invention is to allow a defined gas diffusion to the outer exhaust gas electrode, by arranging the outer pump electrode in its own measurement chamber and by providing a second diffusion barrier with a diffusion coefficient, which differs from the first diffusion barrier's coefficient, in order to determine the pump current in a clear way depending on the exhaust gas composition und thus again to determine the exhaust gas composition from the pump current. Hereby the electronic switching, which produces the pump voltage and the pump current, has to be set out, so that a pole reversal of the pump voltage is possible. By a pole reversal of the pump voltage the diffusion direction of the oxygen or hydrogen in the exhaust gas can be reversed, which allows implications, that are further described in the following, as to the exhaust gas composition.

A single pole reversal of the pump voltage is principally sufficient, in order to make implications about the exhaust gas composition. A particularly advantageous implementation model provides an electronic switching, which produces a rectangular alternating pump voltage. The electronic switching produces a rectangular alternating pump voltage, preferably between 2-500 Hz, especially between 20-50 Hz. By reversing the pump voltage in a rectangular way, an inversion of the pump direction takes place, which delivers qualitative information, whether rich or lean gas exists. The quantity of the current of one of the two pump directions allows a quantitative determination of the concentration.

Principally it is enough if the diffusion coefficient of the second diffusion barrier differs from the one of the first diffusion barrier. One implementation model provides that the diffusion coefficient of the second diffusion barrier is smaller than the diffusion coefficient of the first diffusion barrier. In this case a smaller current is produced at a lean exhaust gas than at a rich exhaust gas. The current is in a way proportional to whether lean or rich exhaust gas exists.

For this purpose the second diffusion barrier can be build more open-pored than the first diffusion barrier.

Another implementation model provides that the second diffusion barrier in the current direction of the exhaust gas shows a shorter duration than the first diffusion barrier.

BRIEF DESCRIPTION OF THE DRAWINGS

Further advantages and characteristics are the subject-matter of the following description as well as of the graphics of implementation models of the invention.

The drawing shows.

DETAILED DESCRIPTION

Figure 1:
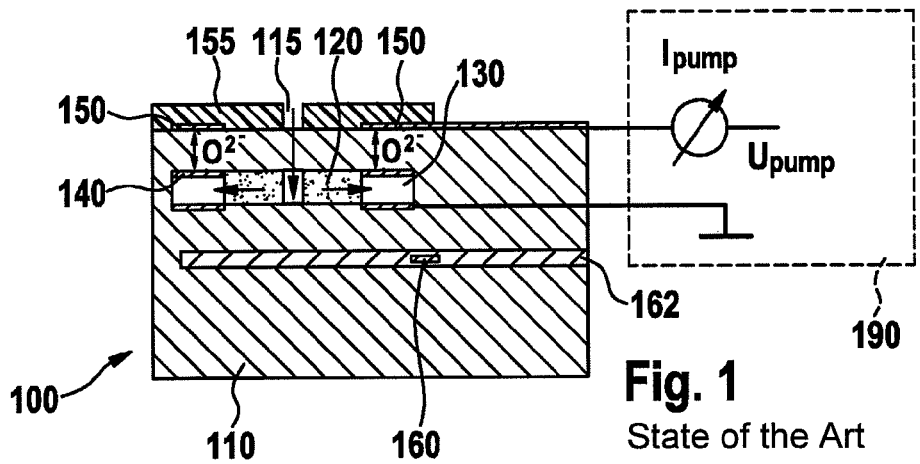
FIG. 1 a gas sensor known from the state of the art.

A gas sensor known from the state of the art shows a sensor element 100, that is produced by a solid electrolyte 110. In the solid electrolyte 110 there is a measurement chamber 130, which contains an inner pump electrode 140. The exhaust gas of a (not further displayed) combustion engine flows through a gas entry leak 115 over a diffusion barrier 120 in the measurement chamber 130. On the outside of the sensor element 100 the exhaust gas is exposes to an outer pump electrode 150, which is covered by an open-pored protective layer 155. An electronic switching 190, that is schematically shown, produces a constant pump voltage $U_{pump}$ between the outer pump electrode 150 and the inner pump electrode 140 that is arranged in the measurement chamber 130. This results at a lean exhaust gas in a positive pump current $I_{pump}$, which leads to the pumping of oxygen ions O2- from the measurement chamber 130 into the outside of the sensor element, that is in the exhaust gas. At a rich exhaust gas composition, that is at a fuel surplus of the exhaust gas, this also leads to a positive pump current due to the decomposing of the water that is in the exhaust gas. The pump voltage is clearly under the decomposing voltage of the water. But since hydrogen exists in the exhaust gas, a water decomposing is energetically possible, for water is produced out of H2 and O2 at the outer pump electrode 150. The current is therefore limited at a rich exhaust gas composition by the hydrogen content at the outer electrode. Because the pump current $I_{pump}$ displays the same direction at a lean and at a rich exhaust gas composition, the exhaust gas composition can not be readily implied from the pump current.

In order to be able to imply the exhaust gas composition also from a rich exhaust gas composition, the invention provides that the outer pump electrode 150 is arranged in a further separate measurement chamber 230, in which exhaust gas flows through the gas entry leak over a second diffusion barrier 220. The second diffusion barrier 220 shows hereby another diffusion coefficient than the first diffusion barrier 120. It is for example build thinner and more open-pored than the first diffusion barrier 120.

The idea of this arrangement is as follows. At lean exhaust gas the current $I_{pump}$ is limited by the diffusion of oxygen to the inner pump electrode 140 (cathode). At a rich exhaust gas composition the pump current $I_{pump}$ is limited by the diffusion of hydrogen to the outer pump electrode 150 (anode). If now the gas supply takes place to the outer pump electrode 150 over a thinner and more open-pored diffusion barrier 220 than the gas supply to the inner pump electrode 140, which takes place over a thicker and less open-pored diffusion barrier, then a reversion of the pump direction has the result, that a lean mix composition lowers the current $I_{pump}$, since the oxygen diffusion limit passes over from the inner pump electrode 140 to the outer pump electrode 150, which is harder to access for the following gas stream. Thereby the electrode, at which the speed determining reaction step, namely the O2-reduction, takes place, is supplied with a lower O2-concentration than before the pole reversal and as a result the current declines.

At a rich exhaust gas composition the pump current $I_{pump}$ is greater, since the hydrogen-diffusion limit passes over from the outer pump electrode 150 (anode) to the inner pump electrode 140 (cathode), which is easier to access by the following gas stream. Hereby the electrode, at which the speed determining reaction step, namely the H2-oxidation to H20, takes place, is supplied with a higher H2-concentration than before the pole reversal and as a result its current rises.

By a pole reversal, the observation of whether the pump current $I_{pump}$ rises or declines, the exhaust gas composition can be qualitatively implied.

The electronic switching 190 performs such a current comparison at a rectangular, high-frequent pole reversal of the pump current $U_{pump}$, that is an inversion of the pump direction. By such a comparison qualitative information can be won, about whether rich or lean gas exists. Because of the quantity of the current $I_{pump}$, a quantitative concentration determination of both pump directions can be undertaken. One implementation model avails oneself, that it is principally sufficient to constantly turn on a positive pump voltage and then, if $I_{pump}=0$ is reached, to produce a short inverting impulse, that is a brief negative pump voltage $U_{pump}$ between the inner pump electrode 140 and the outer pump electrode 150. This inverting impulse then delivers until the next zero-crossing the information whether one is in the lean or rich gas of the engine map.

Figure 2:
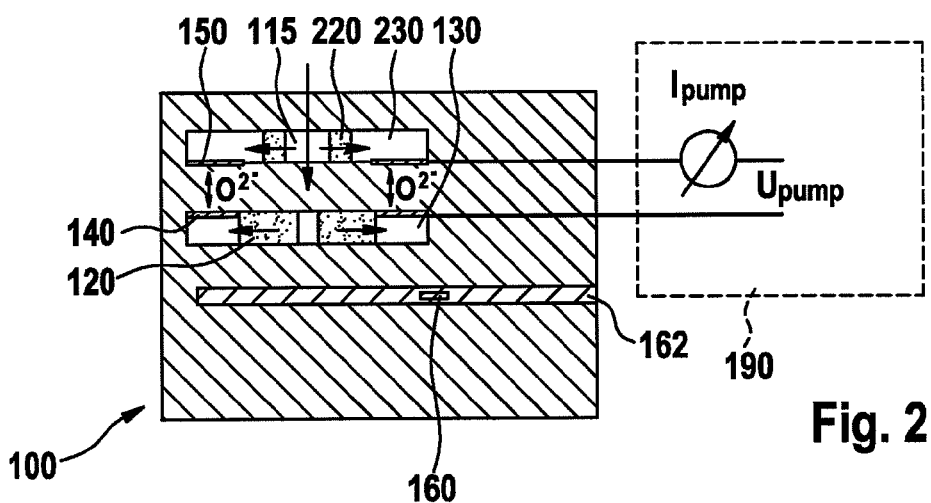
FIG. 2 an implementation model of the invented gas sensor.
Figure 3:
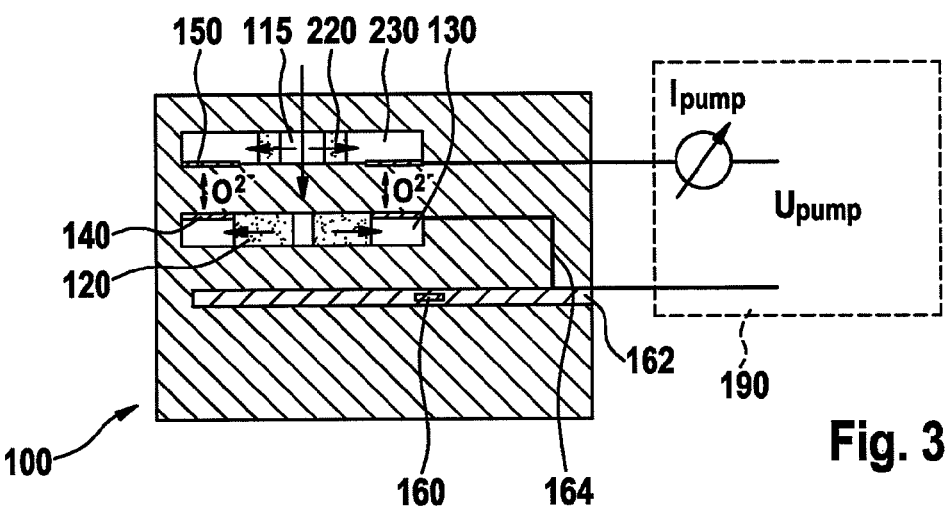
FIG. 3 another implementation model of the invented gas sensor.

In a further advantageous implementation model, that is shown in FIG. 3, the same elements are characterized by the same benchmarks like in the implementation model of FIG. 2, so that their description fully refers to the above-noted.

As opposed to the implementation model in FIG. 2, the implementation model in FIG. 3, the inner pump electrode 140, that is the cathode, is connected to the ground connection of the heating device 160. In this case the potential of the anode, that is the outer pump electrode 150, is alternatively higher and lower than the heating dimension by the quantity of the pump voltage $U_{pump}$. The frequency, which is used to reverse the pump direction, has to be higher than the heating metering in that case, in order to prevent interferences. The advantage of this implementation model, is the omission of a connection cable.

The invention claimed is:

1. A gas sensor, especially a lambda sensor, for determination of an oxygen concentration in an exhaust gas of a combustion engine operated by a fuel-air-mixture, the gas sensor comprising:
   a. a first measurement chamber and a second measurement chamber;
   b. an inner electrode arranged in the first measurement chamber and separated from the exhaust gas by a first diffusion barrier;
   c. an outer electrode arranged in the second measurement chamber and separated from the exhaust gas by a second diffusion barrier; and
   d. an electronic circuit for the production of a voltage between the outer electrode and the inner electrode and for measurement and evaluation of a pump current in order to imply the composition of the fuel-air-mixture;
   wherein a diffusion coefficient of the second diffusion barrier differs from a diffusion coefficient of the first diffusion barrier and wherein the electronic circuit is configured for a repeated pole reversal of the voltage;
   wherein the electronic circuit is configured to measure a first pump current prior to a reversal of voltage polarity and a second pump current after the reversal of voltage polarity,
   wherein the electronic circuit is further configured to compare the first pump current and the second pump current to determine whether a rich gas or a lean gas is present, and wherein the electronic circuit is configured to produce a rectangular alternating pump voltage waveform as the repeated pole reversal of the voltage.

2. A gas sensor according to claim 1, wherein the frequency of the alternating pump voltage waveform is in the range of 2 Hz-500 Hz.

3. A gas sensor according to claim 1, wherein the electronic circuit produces an inverting impulse in the pump voltage waveform after ever a zero-crossing of the pump current.

4. A gas sensor according to claim 1, wherein the diffusion coefficient of the second diffusion barrier is smaller than the diffusion coefficient of the first diffusion barrier.

5. A gas sensor according to claim 1, wherein the second diffusion barrier is more open-pored than the first diffusion barrier.

6. A gas sensor according to claim 1, wherein the second diffusion barrier in a streaming direction of the exhaust gas shows a shorter duration than the first diffusion barrier.

7. A gas sensor according to claim 1, wherein the inner electrode is electrically-conducting connected to a ground connection of a heating device.

* * * * *